United States Patent [19]

Mochida et al.

[11] 4,185,084

[45] Jan. 22, 1980

[54] IMMUNOCHEMICAL MEASURING METHOD USING SECOND ANTIGENIC SUBSTANCE

[75] Inventors: Ei Mochida, Tokyo; Nobuhisa Ogawa, Omiya; Hiroyuki Shinkai, Kawagoe; Masakatsu Hashimoto, Tokyo, all of Japan

[73] Assignee: Mochida Seiyaku Kabushiki Kaisha, Tokyo, Japan

[21] Appl. No.: 838,846

[22] Filed: Oct. 3, 1977

[30] Foreign Application Priority Data

Oct. 7, 1976 [JP] Japan .................................. 51-120623

[51] Int. Cl.$^2$ ............................................. A61K 27/04
[52] U.S. Cl. ...................................... 424/1; 23/230 B;
 23/230.3; 23/230.6; 23/DIG. 16; 435/7;
 424/12; 23/DIG. 21
[58] Field of Search ................ 23/230 B, 230.3, 230.6,
 23/DIG. 16, DIG. 21; 195/103.5 R; 424/1, 12

[56] References Cited

U.S. PATENT DOCUMENTS

| 3,935,074 | 1/1976 | Rubenstein et al. | 424/1 |
|---|---|---|---|
| 3,940,475 | 2/1976 | Gross | 424/1 |
| 3,949,064 | 4/1976 | Bornstein et al. | 424/1 |

*Primary Examiner*—Leland A. Sebastian
*Attorney, Agent, or Firm*—Brisebois & Kruger

[57] ABSTRACT

An immunochemical measuring method using a second antigenic substance and a labeled antibody to the second antigenic substance.

An unknown amount of an antigen (Ag 1) to be measured and a given amount of a conjugate (Ag 1-Ag 2) coupled a second antigen (Ag 2) to the Ag 1 are reacted with a given amount of an antibody (Ab 1) to the Ag 1. Ag 1-Ag 2 bind to the Ab 1 in proportion to their respective amount, forming an Ab 1-Ag 1-Ag 2 complex. Then, by reaction of the complex with a labeled antibody (labeled Ab 2) to the Ag 2, Ab 1-Ag 1-Ag 2-labeled Ab 2 is formed. It is possible to estimate the amount of Ag 1 to be measured by determining the activity of labeled Ab 2 attached to the complex.

9 Claims, 2 Drawing Figures

IMMUNOCHEMICAL MEASURING METHOD USING SECOND ANTIGENIC SUBSTANCE

BACKGROUND OF THE INVENTION

Antigenic substances such as insulin, growth hormone and immunoglobulin are characterized by specificity and sensitivity with which they bind to their antibodies. Utilizing these features, numerous attempts have been made to measure such antigenic substances or their antibodies and in consequence a number of immunochemical measuring processes are now in practical use. For instance, there are; the immunodiffusion methods, in which the antigen and the antibody are reacted together in agar gel; agglulination reaction and agglutination inhibition reaction methods, in which blood cells or fine particles like polystyrene latex are employed as carrier of antigen or antibody; and radioimmunoassay (RIA), in which radioisotopes are employed to label the antigen or the antibody.

Meanwhile, low molecular substances such as steroids, thyroid hormones and active amines, the production of whose antibodies is difficult, used to be measured by the competitive method utilizing the binding reaction of the receptor protein or the binding protein which specifically binds to these substances. Recently, however, the antibodies of these substances have come to be produced with relative ease and accordingly they can now be measured in the same way as the above-mentioned antigenic substances.

These methods have respective characters, by virtue of which they find wide applications. Among others, RIA which is far superior in the sensitivity and quantitative precision of measurement is used widely, the substances measurable by it including a great variety of high molecular substances such as immunoglobulin, virus, protein hormone and low molecular ones such as peptides, steroids.

RIA utilizing radioisotopes, however, demands advanced knowledge and skill from the operator; calls for expensive instruments and facilities; is subjected to many restrictions on account of environment pollution; and for these reasons it fails to find wide applications in clinical practice. Meanwhile, when a substance to be labeled with a radioisotope is, for instance, a low molecular compound like a steroid or an unstable substance like the human placental lactogen, it is difficult to directly label the substance; and even if labeling is possible, the substance is found practically inapplicable due to a decrease or loss of the immunological activity of the substance.

To avoid these inconveniences, lately new processes have been developed such as EIA (enzyme immunoassay) utilizing an enzyme, and FIA (fluorescence immunoassay) utilizing a fluorescent material, instead of a radioisotope. These process are featured by the sensitivity and the quantitative precision of measurement which are approximately equivalent to those of RIA.

RIA, EIA and FIA work on the same principle, i.e., two methods; competitive method and sandwich method. The principle is to be described referring to the case of an antigen being employed as a substance to be measured and an antibody being employed as a substance which specifically binds to the substance to be measured.

1. Competitive method:

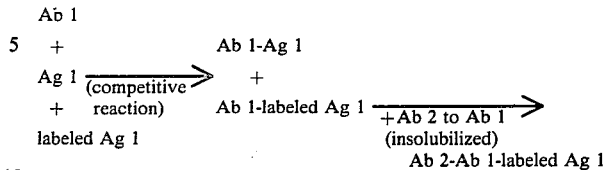

When an unknown amount of an unlabeled antigen (hereinafter referred to as Ag 1) and a given amount of a labeled antigen (hereinafter referred to labeled Ag 1) are caused to react competitively with a given amount of their antibody (hereinafter referred to Ab 1), the Ag 1 and the labeled antigen Ag 1 come to bind to the Ab 1 in proportion to their respective amounts; and accordingly the amount of the labeled Ag 1 to be bound to the Ab 1 is reversely proportional to the amount of the Ag 1. Next, by appropriate means the labeled Ag 1 which has bound to the Ab 1 and the labeled Ag 1 which has not bound to it are separated. The activity of either the labeling agent of the labeled Ag 1 bound or not bound to the Ab 1 is measured. In the meantime, a dilution series of reference substance, whose concentration is known, is prepared and in the same way described above the activity of labeling agent is measured. A standard curve obtained by plotting the measured activities is utilized for determining the amount of the Ag 1 to be measured.

2. Sandwich method

When an unknown amount of an Ag 1 and its Ab 1 which has been made insoluble are reacted together the Ag 1 and the antibody come to bind to each other, forming an Ag 1-Ab 1 complex. Said complex is separated from the reaction mixture and this is caused to react with a given amount of a labeled antibody. Said labeled Ab 1 binds to the complex, but a part of the labeled Ab 1 which exceeds the bindability of said complex remains in a free state in the solution. Then the "bound" labeled Ab 1 and the "free" labeled Ab 1 are separated from each other.

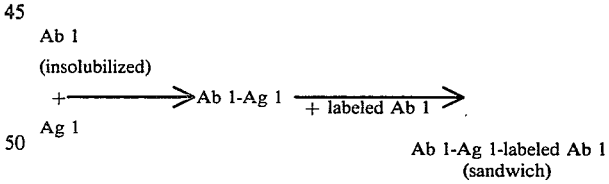

The activity of either the "bound" or the "free" labeling agent is measured. A standard curve is prepared by the same way as described above in competitive method and can be utilized for estimation of the unknown amount of the unlabeled antigen.

SUMMARY OF THE INVENTION

The major object of the present invention is to provide an immunochemical method of measuring physiologically active substances.

Another object of the present invention is to provide a method of measuring with high sensitivity the low molecular and weakly antigenic substances.

Another object of the present invention is to provide the reagents for said immunochemical method of measuring physiologically active substances.

DETAILED EXPLANATION OF THE INVENTION

Figure 1:
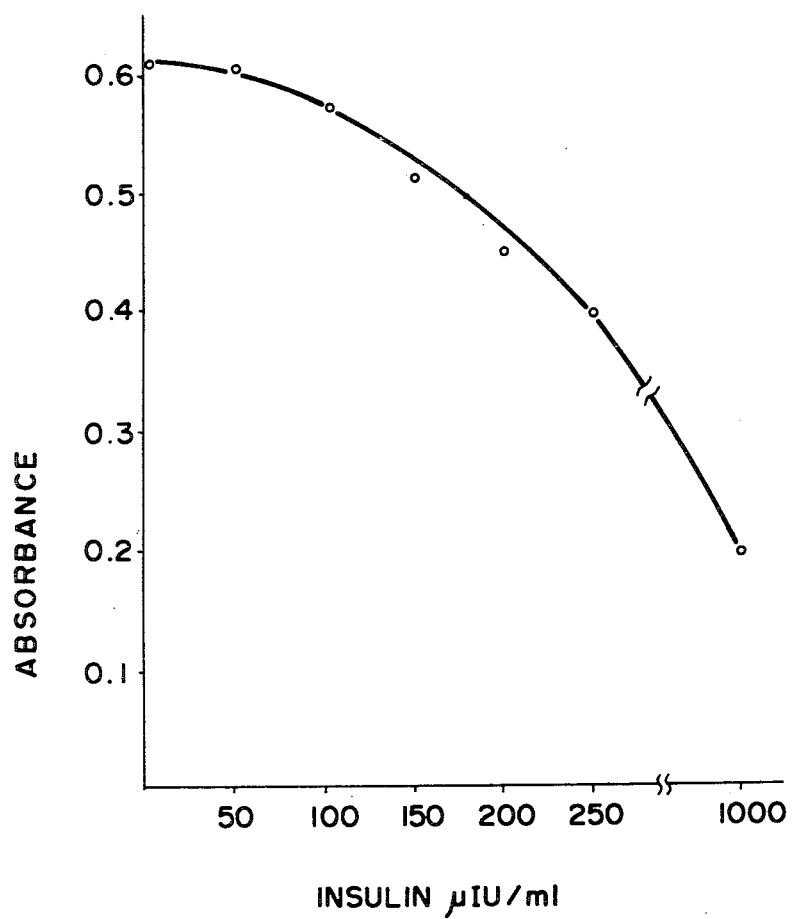
FIG. 1 illustrates a standard curve for insulin measurement in the comparative case 1.

The present invention is a new immunochemical measuring method using a conjugate (Ag 1-Ag 2) coupled an antigen (Ag 1) to be measured to another strongly antigenic substance (Ag 2). The method of the invention comprises the steps of of said competitive method and said saidwich method. Here is to be described the present invention referring to an example using an antigen and its anti-body.

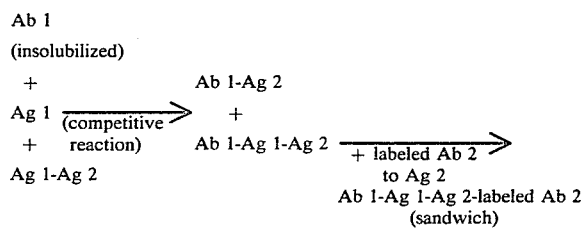

An unknown amount of an unlabeled antigen (Ag 1) to be measured and a given amount of an antigen conjugate, (Ag 1-Ag 2) in which Ag 2 is another antigenic substance are caused to competitively react with a given amount of the antibody Ab 1 to the Ag 1. Since the Ag 1 and Ag 1-Ag 2 conjugate bind to the Ab 1 in proportion to their respective amounts, the amount of the Ag 1-Ag 2 conjugate to be bound to the Ab 1 is reversely proportional to the amount of the Ag 1. After separating the Ab 1-Ag 1-Ag 2 complex formed in the above reaction, the complex is caused to react with a given amount of a labeled antibody (hereinafter referred to labeled Ab 2) to the Ag 2. The labeled Ab 2 binds to the Ab 1-Ag 1-Ag 2 complex and forms an Ab 1-Ag 1-Ag 2-labeled Ab 2 like a sandwich. The labeled Ab 2 in the reaction mixture is then separated into the "bound" labeled Ab 2 and the "free" labeled Ab 2. The activity of the labeling agent of the labeled Ab 2 either in the "bound" fraction or in the "free" fraction is measured. From a standard curve prepared by the performance run parallely in the same time with a reference substance, the unknown amount of the Ag 1 to be measured is estimated.

In the above case, the substance to be measured is an antigen and the bindable substance is its antibody. The present invention, however, is applicable to the case of the substance to be measured being an antibody and the bindable substance being its antigen; and even to the hapten-antibody system or physiologically active substance-receptor protein or binding protein system as well as to a complete antigen-antibody system.

Various animal serum proteins such as alubumin, globulin; and strongly antigenic substances such as human chorionic gonadotropin (HCG), hemoglobin, tetanus toxoid, pnumococcal polysaccharide, glutamic acid-lysine-tyrosine copolymer may be available as Ag 2 to be coupled to the substance (Ag 1) to be measured, but it would be advantageous to use a glycoprotein like HCG, as explained later.

The method to make a Ag 2 coupled to the Ag 1 differs depending on the properties of the Ag 1 and Ag 2. For instance, the second antigen can be coupled to protein by various known methods such as: methods using an amino group of protein as the binding site (diisocyanate method, maleic anhydride method, glutaraldehyde method, formic acid analogue method); a method using an SH group as the binding site (divalent mercury compound method); a method using a tyrosin or histidine group as the binding site (diazo compound method) or a method using a carboxylic group as the binding site (carbodiimide method). Meanwhile, for the purpose of causing the Ag 2 to couple to a hapten such as a steroid, hemisuccinate method or oxime method is available. If a glycoprotein like HCG is employed as Ag 2, it will be possible to cause coupling with use of an aldehyde group obtained through oxidation of its sugar chain. This method is found satisfactory because it excels in binding efficiency and inflicts little damage to the substance which couples to Ag 2.

The Ab 2 to an Ag 2 can be prepared by routine method through immunization of a rabbit or a goat.

As the agent to label the Ab 2, the following materials may be available: radioisotopes (for instance, $^{125}$I, $^{131}$I, $^{3}$H, $^{14}$C); enzymes (for instance, horseradish peroxidase, $\beta$-D-galactosidase, alkaline phosphates, glucose oxidase, glucoamylase); or fluorescent materials (for instance, fluorescein isothiocyanate, rhodamine).

For the purpose of labeling the Ab 2 with such agents, the following methods are available: chloramine T method (F. C. Greenwood and W. M. Hunter; Nature, 194, 495 (1962)); periodate method (P. Nakane and A. Kawaoi; J. Histochem. Cytochem., 22, 1084 (1974)) and others.

For the purpose of separating an Ag 1-Ag 2 conjugate which has bound to the Ab 1 from an Ag 1-Ag 2 conjugate which has not done so, or separating a labeled Ab 2 which has bound to the Ag 1-Ag 2 conjugate from a labeled Ab 2 which has not done so, many methods in the prior art are available such as: methods of chromatography, electrophoresis, salting out, alcoholic precipitation, gel filtration, solid phase and double antibody; but for reason of simplicity of operation, it would be advantageous to adopt the solid phase method in which an antibody is bound to an insoluble carrier.

As compared with the conventional methods, the present invention has the following outstanding features.

It is well-known that the relatively low molecular substances such as insulin, adrenocorticotropic hormone, glucagon, gastrin are weakly antigenic; and with low reactivity to the labeled antibody, these substances bind to only a small amount of the labeled antibody. In order to increase the binding amount of the labeled antibody, in the present invention, a strongly antigenic substance is coupled to the substance to be measured; thereby the substance to be measured can be caused to bind a large amount of said labeled antibody due to the high bindability said second antigen. Thus according to the present invention, the measurement can be performed with a higher sensitivity than that according to the conventional method, even if the amount of the substance to be measured is extremely small.

Moreover the present invention has such a merit that if the Ag 2 to be coupled to the Ag 1 is confined to a single material which can result in the best measuring, only one kind of labeled Ab 2 will suffice and therefore it will be needless to prepare various labeled antibodies corresponding to different substances to be measured.

The measurable substances by the present invention include low molecular substances, for instance, steroids such as testosterone, setriol, progesterone, corticosterone, aldosterone; thyroid hormones such as thyroxine, triiodothyronin; physiologically active peptides such as bradykinin, angiotensin, thyroid hormone-releasing hormone, luteinizing hormone-releasing hormone; physiologically active amines such as epinephrine, norepinephrine, histamin, serotonin; prostglandin; relatively low molecular substances, for instance, insulin, glucagon, adrenocorticotropic hormone, gastrin; and high molecular substances, for instance, human chorionic gonadotropin, growth hormone, human placental lactogen, immunoglobulin E, α-fetoprotein, hapatitis B antigen.

The following examples further illustrate the invention.

COMPARATIVE EXAMPLE 1-MEASUREMENT OF INSULIN (COMPETITIVE METHOD)

(a) Preparation of standard insulin solution

Bovine crystal insulin (Sigma Chemical, 25 IU/mg) was dissolved to concentrations of $10^4$, $10^3$, 320, 80, 20 and 0 μIU/ml in a phosphate buffered saline (PBS, pH 6.4) containing 0.1% bovine serum albumin (BSA).

(b) Preparation of anti-insulin antibody

Bovine crystal insulin suspended in physiological saline; thereafter dissolved by adding 0.1 N hydrochloric acid drop by drop and adjusted to a concentration of 2 mg/ml. The insulin solution was mixed with activated charcoal powder (Wako Pure Chemical) at a rate of 10 mg to 1 ml of said insulin solution, thereby causing insulin to be adsorbed on the activated charcoal. The insulin adsorbed charcoal was centrifugally separated. By adding 0.5 ml of physiological saline to 10 mg of this activated charcoal, the insulin adsorbed activated charcoal suspension was obtained. A guinea pig was injected every other week a mixture of 0.25 ml of this suspension and 0.25 ml of Freund's complete adjuvant and the injection was repeated 10 times. One week after the final injection, the blood was collected from the animal's carotid, thereby producing a guinea pig anti-insulin serum. The antiserum thus obtained was salted out two times with sodium sulfate and the anti-insulin antibody was obtained.

(c) Preparation of insulin-horseradish peroxidase conjugate

According to P. Nakane—A. Kawaoi's periodate method, bovine crystal insulin was bound to horseradish peroxidase. Namely, 5 mg of horseradish peroxidase (HRP) was dissolved in 1 ml of 0.3M sodium bicarbonate, followed by addition of 0.1 ml of 1% 2,4-dinitrofluorobenzene. The mixture obtained was stirred for one hour at room temperature. Next, 1 ml of 0.08 M sodium periodate was added thereto and mixed for 30 minutes at room temperature, followed by addition of 1.0 ml of 0.16 M ethyleneglycol and mixing for one hour at room temperature. The obtained solution was submitted to dialysis overnight against 0.01 M sodium carbonate buffer, pH 9.5; then added thereto 1.0 ml of insulin solution obtained by dissolving bovine crystal insulin to a concentration of 5 mg/ml in 0.01 M sodium carbonate buffer, pH 9.5; and after reaction for three hours at room temperature, 5 mg of sodium borohydride was added to the reaction mixture, followed by standing for three more hours at 4° C. After the reaction, dialysis overnight against PBS, pH 7.2, was done and then followed by fractionation and purification with Sephadex G-200 and lyophilization, thereby producing an insulin-horseradishperoxidase conjugate (INS-HRP).

(d) Preparation of rabbit anti-guinea pig γ-globulin antibody coupled cellulose

A healthy guinea pig serum was purified by salting out and DEAE cellulose column chromatography, yielding a γ-globulin fraction. The obtained guinea pig γ-globulin fraction was dissolved to a concentration of 2 mg/ml in physiological saline; 0.5 ml of the obtained solution was mixed with 0.5 ml of Freund's complete adjuvant; a rabbit was injected the mixture 5 times, one a week; one week after the final injection, blood was collected from the rabbit and thus the rabbit anti-guinea pig γ-globulin serum was obtained. The obtained antiserum was purified by salting out, producing the rabbit anti-guinea pig γ-globulin antibody.

Eight g of cellulose powder (Merk Chemical) was added to 320 ml of 2.5% cyanogen bromide. The suspension was adjusted to pH 10–11 by 1 N sodium hydroxide, followed by reaction for two minutes under stirring. Then the suspension was passed through a glass filter and washed with 0.1 M sodium bicarbonate, producing an activated cellulose. The activated cellulose was suspended in 32 ml of 0.1 M sodium bicarbonate; and to this suspension was added 8 mg of the rabbit anti-guinea pig γ-globulin antibody, followed by standing for 22 hours at 4° C. under stirring. After the reaction, the suspension was washed with PBS, pH 6.4, and a mixture, pH 7.0, of 8 M urea and 0.2 M glycine and suspended to a concentration of 10% in PBS, pH 6.4, containing 1% BSA.

(e) Measurement of insulin

One tenth ml of standard insulin solution of each concentration obtained in (a) was put in a test tube and to this tube was added 0.1 ml of the anti-insulin antibody in (b) as a solution diluted 16,000 times with PBS; and this was followed by incubation for 50 minutes at room temperature. To the solution was then added 0.1 ml of INS-HRP in (c) as a solution diluted 30 times with PBS and this was followed by incubation for 40 minutes at room temperature. Next, 0.1 ml of 10% suspension of the rabbit anti-guinea pig γ-globulin antibody coupled cellulose obtained in (d) was added and the suspension was incubated for 90 minutes. The solid phase, after centrifugal separation of the liquid phase, was washed two times with physiological saline containing Tween 20. Then 3 ml of a substrate solution containing 5-aminosalicylic acid of 60 mg/dl and 3% hydrogen peroxide of 100 μl/dl was added, following by incubation for one hour at room temperature. After addition of two drops of 1.6% sodium azide, the absorbance at 465 nm was measured. The standard curve prepared thereby is illustrated in FIG. 1. From FIG. 1, 50 μIU/ml of insulin can be measured.

COMPARATIVE EXAMPLE 2-MEASUREMENT OF INSULIN (SANDWICH METHOD)

(a) Preparation of antibody-sensitized polystyrene test tube

The anti-insulin antibody obtained in Case 1-(b) was dissolved to a concentration of 100 μg/ml in glycine buffer, pH 8.2; and 1 ml of the solution was put in a polystyrene test tube of 1.5 cm inner diameter and 10 cm length and the test tube was incubated for three hours at 37° C. The tube was washed with physiological saline, added 1% normal guinea pig serum-PBS and left overnight at 4° C., producing an anti-insulin antibody-sensitized polystyrene test tube.

(b) Preparation of anti-insulin antibody-HRP conjugate

In accordance with the method of Case 1-(c), reaction was caused between 5 mg of the anti-insulin antibody in Case 1-(a) and 5 mg of HRP, producing an anti-insulin antibody-HRP conjugate.

(c) Measurement of insulin

In the anti-insulin antibody-sensitized polystyrene test tube prepared in (a), 0.1 ml of the standard insulin solution of each concentration obtained in Case 1-(a) was put and then it was incubated for one hour. Next after the solution was thrown away, the tube was washed with physiological saline. After 0.1 ml of the anti-insulin antibody-HRP conjugate manufactured in (b) was added into the tube, it was left for one hour at room temperature. After the reaction, the tube was washed with physiological saline. Then addition of 3 ml of a substrate solution containing 5-aminosalicylic acid of 60 mg/dl and 0.3% hydrogen peroxide of 1 ml/dl was made and it was left for one hour at room temperature. Thereafter the absorbance at 465 nm was measured. From the standard curve prepared thereby, 20–30 μIU/ml of insulin can be measured.

EXAMPLE 1-MEASUREMENT OF INSULIN (a) Preparation of insulin-HCG conjugate

Five mg of HCG was dissolved in 1 ml of 0.3 M sodium bicarbonate and added thereto 0.1 ml of 1% 2,4-dinitrofluorobenzene, followed by standing for one hour at room temperature. Subsequently in accordance with the method in Case 1-(c), an insulin-HCG conjugate (INS-HCG) was obtained.

(b) Preparation of anti-HCG antibody

HCG was injected into a rabbit by routine method to obtain the rabbit anti-HCG serum. The antiserum was salted out by sodium sulfate, thereby producing an anti-HCG antibody.

(c) Preparation of anti-HCG antibody-HRP conjugate

In accordance with the method in Case 1-(c), reaction was caused between 5 mg of anti-HCG antibody obtained in (b) and 5 mg of HRP, producing an anti-HCG antibody-HRP conjugate.

(d) Preparation of anti-insulin antibody-sensitized polystyrene test tube

The anti-insulin antibody obtained in Case 1-(b) was dissolved to a concentration of 20 μg/ml in glycine buffer, pH 8.2. In a polystyrene test tube was put 1 ml of the solution and it was incubated for 30 minutes in water bath of 56° C. Thus an anti-insulin antibody-sensitized polystyrene test tube was prepared.

(e) Measurement of insulin

Figure 2:
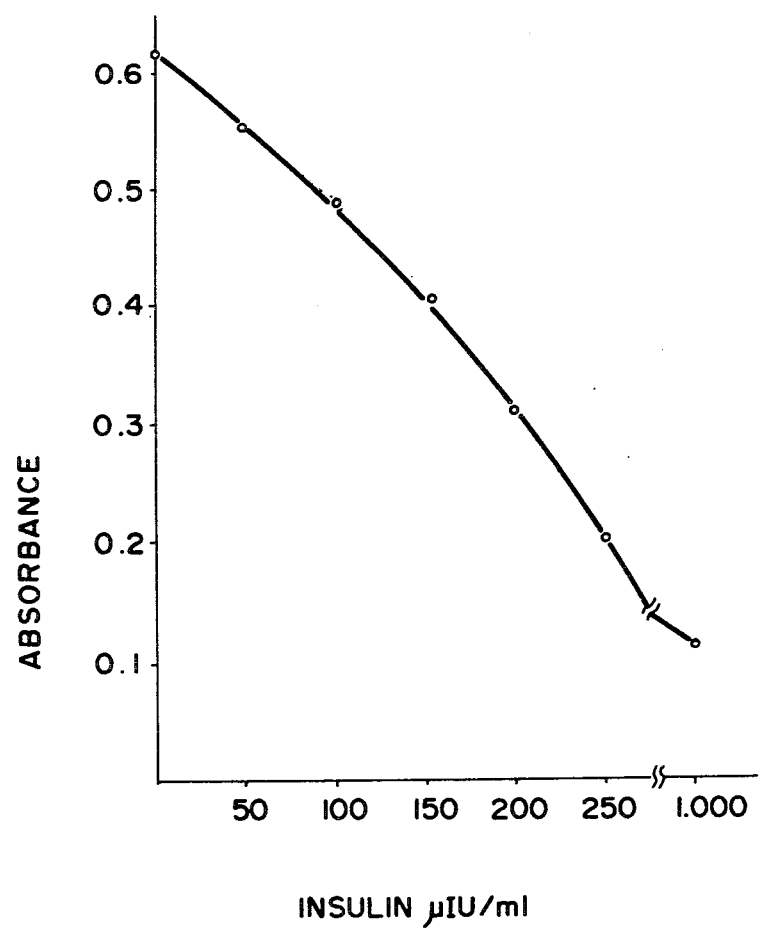
FIG. 2 illustrates a standard curve for insulin measurement in the example of execution 1.

In the anti-insulin antibody-sensitized polystyrene test tube prepared in (d), 0.4 ml of each standard insulin solution obtained in Case 1-(a) and 0.3 ml of 0.5% BSA were added and the mixture was incubated for 18 hours at 4° C. Then 0.1 ml of INS-HCG solution obtained in (a) was added, following by incubation for one hour at 37° C. After the incubation, the solution in the test tube was removed and the tube was washed with phosphate buffer and then 0.1 ml of the anti-HCG antibody-HRP conjugate obtained in (c) and 0.7 ml of 0.5% BSA were added and the mixture was incubated for one hour at 37° C. After washing the test tube, 3 ml of a substrate solution containing 5-aminosalicylic acid of 60 mg/dl and 3% hydrogen peroxide of 100 μl/dl was added, following by reaction for one hour at room temperature, after which the absorbance at 465 nm was measured. The standard curve prepared thereby is illustrated in FIG. 2. It is apparent that measurement of 10 μIU/ml of insulin is found possible from FIG. 2. This measurement is 3–5-fold more sensitive than that of the conventional method.

EXAMPLE 2-MEASUREMENT OF INSULIN (a) Preparation of insulin-BSA conjugate

Ten mg of bovine crystal insulin and 12.8 mg of BSA were dissolved respectively in 10 ml of 0.4 M borate buffer, pH 9.0, and these two solutions were mixed. To the obtained mixture was added 0.37 ml of 0.01 M bis-diazobenzidine and it was left for one hour at room temperature under stirring. After the reaction, the solution was concentrated by a ultrafiltration method, followed by purification with Sephadex G-150, producing an insulin-BSA conjugate.

(b) Preparation of radioactive iodine-labeled anti-BSA antibody

In a small test tube 0.25 ml of 0.5 M phosphate buffer was put and thereto was added 2 mCi of radioactive sodium iodide ($Na^{131}I$). Next 0.025 ml of 400 μg/ml anti-BSA antibody solution prepared and purified by a conventional means and 0.02 ml of 4 mg/ml chloramine T were added and mixed together for one minute. Thereupon, 0.1 ml of 24 mg/ml sodium metabisulfite and then 0.4 ml of 10 mg/ml potassium iodide were added. The reaction mixture was purified with Sephadex G-50, producing $^{131}I$-anti-BSA antibody.

(c) Measurement of insulin

In an anti-insulin antibody-sensitized polystyrene test tube prepared in Case 2-(a), 0.1 ml of each standard insulin solution obtained in Case 1-(a) and 0.6 ml of PBS solution of 0.1% rabbit γ-globulin (RGG) were added and incubated for 18 hours at 4° C. Then 0.1 ml of the insulin-BSA conjugate obtained in (a) was added thereto, following by incubation for one hour at 37° C. After the incubation, the solution was removed and the test tube was washed with phosphate buffer three times and then 0.1 ml of radioactive iodine-labeled anti-BSA antibody solution obtained in (b) and 0.7 ml of PBS containing 0.1% RGG were added and the mixture was incubated for one hour at 37° C. After removal of the reaction mixture, the test tube was washed and using a scintillation counter the residual radioactivity in the test tube was measured. According to this method, 1 μIU/ml of insulin can be measured.

EXAMPLE 3-MEASUREMENT OF HUMAN PLACENTAL LACTOGEN (HPL)

(a) Preparation of standard HPL solution

In accordance with H. Morikawa and other's method (H. Morikawa, et al., Jap. J. Endocrinol., 49, 882 (1973)), HPL extracted and purified from placenta of delivery of a normal pregnant woman was dissolved to concentrations of 100, 10, 2.5, 0.6, 0.15 and 0 ng/ml in PBS, pH 6.4, containing 0.1% BSA.

(b) Preparation of HPL-HCG conjugate

In accordance with the method in Case 1-(c), 5 mg of HCG and 5 mg of HPL were reacted together, producing an HPL-HCG conjugate.

(c) Preparation of anti-HPL antibody coupled cellulose

A rabbit anti-HPL serum obtained from a rabbit immunized against HPL was purified by salting out to produce an anti-HPL antibody. In accordance with the method in Case 1-(d), the antibody thus obtained was reacted with cellulose, producing an anti-HPL antibody coupled cellulose and then lyophilized.

(d) Measurement of HPL

In a test tube, 0.5 ml of 1% suspension of the anti-HPL antibody coupled cellulose obtained in (c) and 0.1 ml of each standard HPL solution obtained in (a) were put together, and the mixture was incubated for one hour at 37° C. Then to the mixture was added 0.1 ml of HPL-HCG conjugate obtained in (b) and was incubated for one hour at 37° C. After the incubation, the anti-HPL antibody coupled cellulose was separated and was washed with phosphate buffer. Then 0.1 ml of the anti-HCG antibody-HRP conjugate obtained in example 1-(c) and 0.6 ml of 0.5% BSA were added, following by incubation for one hour at 37° C. Thereafter, washing with phosphate buffer was done and this was followed by addition of 3 ml of a substrate solution containing 5-amino-salicylic acid of 60 mg/dl and 0.3% hydrogen peroxide of 1 ml/dl and was left for one hour at room temperature. Thereupon, the absorbance at 465 nm was measured. According to this method, 0.5–1 ng/ml of HPL can be measured.

EXAMPLE 4-MEASUREMENT OF ESTRIOL (a) Preparation of standard estriol solution

Estriol (Sigma Chemical) was dissolved for concentrations of 640, 160, 40, 10, 2.5 and 0 ng/ml in PBS, pH 6.4, containing 0.1% BSA.

(b) Preparation of estriol-16,17-dihemisuccinate-BSA conjugate

Six hundreds mg of estriol-16,17-dihemisuccinate (Am. J. Obstet. Gynecol., 109, 897, (1971)) was dissolved in 12 ml of dioxane and then 0.3 ml of tri-n-butylamine was added to the solution. Cooled to 12° C., to the solution was added 0.17 ml of isobutylchlorocarbonate and it was mixed well by stirring. To the mixture thus obtained was mixed with a solution obtained by dissolving BSA 1.70 g in 40 ml of distilled water, adjusting the solution to pH 12.0 with use of 1 N solium hydroxide, adding 40 ml of dioxane to it and then kept at 12° C. After reaction for 4 hours under stirring, unreacted low molecular substances such as estriol-16,17-dihemisuccinate, tri-n-butylamine were separated with use of Sephadex G-25. The high molecular fraction was lyophilized, thereby an estriol-16,17-dihemisuccinate-BSA conjugate was obtained.

(c) Preparation of estron-17-oxime-hemoglobin conjugate

In 20 ml of dioxane 687 mg of estron-17-oxime (Erlanger, B. F., J. Biol. Chem., 234, 1090 (1959)) was dissolved. To the solution obtained was added 0.9 ml of tri-n-butylamine. Then cooled to 11° C., to the solution was added 0.27 ml of isobutylchlorocarbonate and it was stirred. To this mixture was added a solution obtained by dissolving 2.42 g of hemoglobin (Hb) in 70 ml of distilled water, adjusting it to pH 9.5 and then adding 70 ml of dioxane, and it was kept at 11° C. After reaction for 4 hours under stirring, unreacted low molecular substances were separated with use of Sephadex G-25. The high molecular fraction was lyophilized, thereby an estron-17-oxime-Hb conjugate was obtained.

(d) Preparation of anti-Hb antibody-HRP conjugate

A goat was injected each time 20 mg of Hb together with Freund's complete adjuvant 3-4 times every other week and in accordance with the method in Case 1-(b) an anti-Hb antibody globulin was obtained. Reaction between 5 mg of this anti-Hb antibody globulin and 5 mg of HRP was caused by the method of Case 1-(c), producing an anti-Hb antibody-HRP conjugate.

(e) Preparation of anti-estriol antibody

The estriol-16,17-dihemisuccinate-BSA conjugate obtained in (b) was dissolved in physiological saline. The solution, together with Freund's complete adjuvant, was subcutaneously injected into the back of an adult rabbit repeatedly, 2 mg of said conjugate each time. After a rise of the antibody titer was confirmed, blood was collected, yielding an anti-estriol-16,17-dihemisuccinate-BSA antibody by the method in Case 1-(b). Using BSA which had been coupled with Sepharose by by cyanogen bromide, the anti-BSA antibody was removed from this antibody. Namely, after addition of BSA coupled Sepharose at a rate of 25 ml to 50 ml of the antibody solution, the suspension was left for 30 minutes at 37° C., followed by incubation overnight at 4° C. Then the suspension was centrifuged for 10 minutes at 4° C., producing a specific antibody to estriol.

(f) Measurement of estriol

In an anti-estriol antibody-sensitized polystyrene test tube prepared by the method in Case 2-(a), a 0.6 ml of 0.1% BSA and 0.1 ml of standard estriol solution in (a) were added together and were incubated for one hour at room temperature. Then 0.1 ml of the estron-17-oxime-Hb conjugate prepared in (c) was added to the solution and was incubated for one hour at room temperature. After the reaction, washing with phosphate buffer was done. Next, 0.1 ml of the anti-Hb antibody-HRP conjugate obtained in (d) and 0.5 ml of 0.1% BSA were added thereto and were incubated for one hour at room temperature, followed by washing. Thereafter, 3 ml of a substrate solution in Example 1 was added and it was left for one hour at room temperature. Then the absorbance at 465 nm was measured. According to this method, 1 ng/ml of estriol can be measured.

EXAMPLE 5-MEASUREMENT OF INSULIN (a) Preparation of rat liver insulin receptor

Rat liver insulin receptor was prepared according to K. Suzuki and other's method (K. Suzuki, et al.; Saishin Igaku, 30, 591 (1975)).

(b) Preparation of insulin-HCG conjugate

In accordance with the method in Example 1-(a), an insulin-HCG conjugate was obtained.

(c) Preparation of $^{125}I$ labeled anti-HCG antibody

The anti-HCG antibody obtained in Example 1-(b) was labeled with $^{125}I$ by the chloramine T method. The labeled antibody was purified with Sephadex G-50, producing an $^{125}I$-anti-HCG antibody.

(d) Measurement of insulin

In a test tube, 0.1 ml of standard insulin solution in Case 1-(a), 0.5 ml of 0.5% BSA and 0.1 ml of the receptor suspension in (a) were added together, following by incubation for one hour at 4° C. Next, in the test tube was added 0.1 ml of the insulin-HCG conjugate in (b) and then it was left overnight at 4° C. Then the reaction mixture was centrifuged and the precipitate receptor was washed with a cold phosphate buffer; and then in the tube was put 0.5 ml of 0.5% BSA and 0.1 ml of the $^{125}I$-anti-HCG antibody solution in (c) were added and the mixture was left overnight at 4° C. Thereupon, after centrifuging and washing phosphate buffer, the radioactivity of the precipitated receptor was measured. According to this method, more than 5 ng/ml of insulin can be measured.

What is claimed is:

1. An immunochemical measuring method comprising the steps of
   (a) reacting an antibody to an antigen to be measured (Ab 1) with an antigen to be measured (Ag 1) and a conjugate coupled with said antigen to be measured to a second antigen having strong antigenicity (Ag 1-Ag 2),
   (b) separating the Ab 1-Ag 2 complex produced by the above reaction from the reaction mixture,
   (c) reacting the separated Ab 1-Ag 1-Ag 2 complex with a labeled antibody to the second antigen (Ab 2),
   (d) separating the reaction products of Ab 1-Ag 1-Ag 2-labeled Ab 2 complex produced by the above reaction from the reaction mixture, and
   (e) measuring either the activity of a labeling agent bound to the above reaction products or of a labeling agent remaining in the reaction mixture.

2. Immunochemical measuring method of claim 1, wherein the antigen to be measured is selected from the group consisting of low molecular substances, relatively low molecular substances and high molecular substances.

3. Immunochemical measuring method of claim 1, wherein the second antigen is selected from the group consisting of bovin serum albumin, human serum albumin, rabbit γ-globulin, human chorionic gonadotropin, hemoglobin, tetanus toxoid, pneumococcal polysaccharide or glutamic acidlysinetyrosine copolymer.

4. Immunochemical measuring method of claim 1, wherein the labeling agent is selected from the group consisting of radioisotope, enzyme or fluorescent material.

5. Reagent for immunochemical measurement, comprising a bindable substance which specifically binds to a substance to be measured; an antigen conjugate of the substance to be measured which has been bound to a substance having high antigenicity; and a labeled antibody of the substance having high antigenicity.

6. The reagent for immunochemical measurement of claim 5, wherein the substance to be measured include a low molecular substances, relatively low molecular substances and high molecular substances.

7. The reagent for immunochemical measurement of claim 5, wherein the substance having high antigenicity is bovine serum albumin, human serum albumin, γ-globulin, human chorionic gonadotropin, hemoglobin, tetanus toxoid, pneumococcal polysaccharide or glutamic acid-lysine-tyrosine copolymer.

8. The reagent for immunochemical measurement of claim 5, wherein the labeling agent is radioisotope, enzyme or fluorescent material.

9. The reagent for immunochemical measurement of claim 5, wherein the bindable substance, the antigen conjugate and the labeled antibody are lyophilized.

* * * * *